United States Patent [19]

Butz et al.

[11] Patent Number: 4,533,373
[45] Date of Patent: Aug. 6, 1985

[54] SEPARATION OF $CO_2$ AND $H_2S$ FROM HYDROGEN CONTAINING GAS

[75] Inventors: Peter Butz, Munich; Gerhard Ranke, Poecking; Tran A. Tvan, Neuried, all of Fed. Rep. of Germany

[73] Assignee: Linde Aktiengesellschaft, Wiesbaden, Fed. Rep. of Germany

[21] Appl. No.: 500,697

[22] Filed: Jun. 3, 1983

[30] Foreign Application Priority Data

Dec. 23, 1982 [DE] Fed. Rep. of Germany ....... 3247773

[51] Int. Cl.$^3$ ................................................ F25J 3/02
[52] U.S. Cl. ............................................ 62/17; 55/68; 55/73
[58] Field of Search .......................... 62/17, 20, 23–28; 208/337, 348, 351, 355, 358; 55/68, 73

[56] References Cited

PUBLICATIONS

"Pilot Tests Prove Ryan/Holmes Cryogenic Acid Gas/Hydrocarbon Separation"; 61st Annual GPA Convention; Holmes et al., Reprint Mar. 15–17, 1982.

Primary Examiner—Frank Sever
Attorney, Agent, or Firm—Millen & White

[57] ABSTRACT

For the purification of hydrocarbon-containing, e.g., methane raw gases containing $H_2S$ and $CO_2$, the raw gas is dried, and separated by rectification into a hydrocarbon-rich overhead fraction containing some $H_2S$ and $CO_2$ and into a bottom fraction consisting essentially of $H_2S$ and $CO_2$. The overhead product is freed, in a first scrubbing column, of the acidic components with a physical acting scrubbing medium selective for $H_2S$ and COS as against $CO_2$, e.g., polyethylene glycol ether or toluene. The bottom product from the rectification step is vaporized and selectively desulfurized in a second scrubbing column with the same scrubbing medium, and the scrubbed gas from the second scrubbing column is discharged as $CO_2$ under pressure.

23 Claims, 1 Drawing Figure

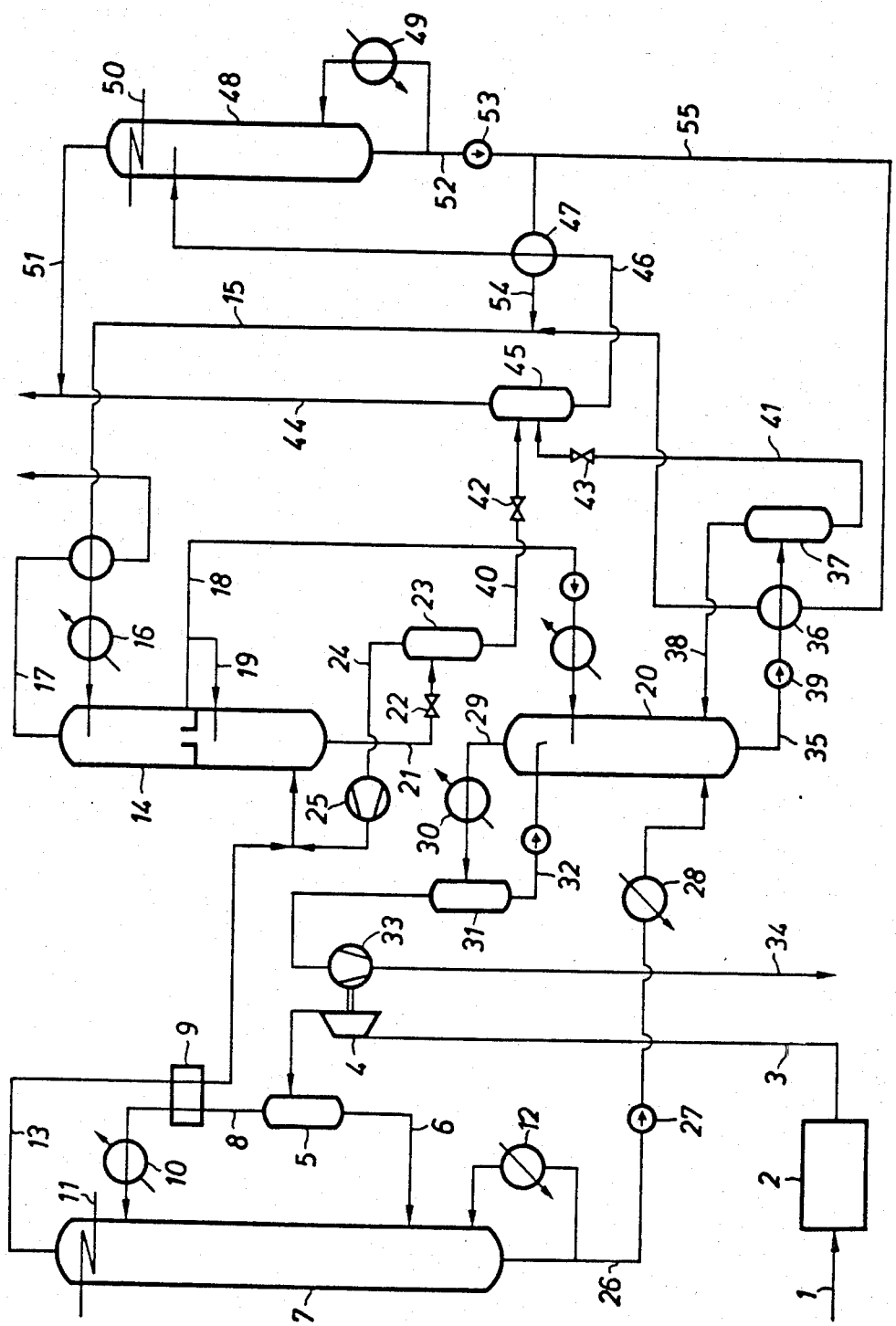

SEPARATION OF CO₂ AND H₂S FROM HYDROGEN CONTAINING GAS

BACKGROUND OF THE INVENTION

This invention relates to a gas absorption process for the removal of acidic components, especially $CO_2$ and $H_2S$ and, in some cases, COS, from $CO_2$-rich, hydrocarbon-containing raw gases wherein the raw gas is scrubbed under pressure with a physical scrubbing medium selective for $H_2S$ and COS; and the resultant loaded scrubbing agent is then regenerated and reused.

Is is conventional to remove sour gases, e.g., $CO_2$, $H_2S$, and COS from gaseous mixtures by the use of scrubbing processes. In this connection, physical, i.e., no chemical reaction, scrubbing procedures have been utilized as well as chemical. The physical scrubbing processes operate most efficiently under a high total pressure and with a high sour gas concentration. However, a disadvantage with physical scrubbing processes occurs when there is the simultaneous presence of hydrocarbons which have a similarly high solubility as the sour gases in the scrubbing agent.

Physical scrubbing processes already in use employ, e.g., as the absorbents, polyethylene glycol ether, N-methylpyrrolidone, or propylene carbonates (e.g., Oil and Gas Journal No. 40, October 1982, pages 90–93). In most cases, these scrubbing processes are employed to remove the acidic components from natural gases to such an extent that the purified gas can subsequently be utilized as fuel gas. Usually, $H_2S$ from the sour gases is reacted to elemental sulfur and the $CO_2$ is exhausted into the atmosphere.

Besides the use of scrubbing methods, sour gases are removed from gaseous mixtures by liquifaction and subsequent rectification. To avoid precipitation of $CO_2$ durint cooling and rectification, it is suggested in the prior art to add a suitable solvent, such as a lighter hydrocarbon, preferably propane. In this way, $CO_2$ and $H_2S$ can be separated by rectification into $H_2S$-free $CO_2$ and into concentrated $H_2S$ and solvent. A serious disadvantage of this process, however, resides in that $H_2S$ and the above-mentioned solvent cannot be economically separated cleanly from each other by rectification. Accordingly, a chemical scrubbing step must be used to remove the $H_2S$ from the vaporized solvent. This involves the drawback that a relatively large amount of vapor must be used for the regeneration of the liquor, and, simultaneously, the solvent required for rectification must additionally be subjected to a drying step. Such a process is described e.g. in the paper presented at 61st Annual GPA Convention March 15–17, 1982, Dallas, Tex.

SUMMARY OF THE INVENTION

An object of the present invention is to provide a process avoiding the aforementioned disadvantages and making it possible to obtain, besides a fuel gas complying with commercial specifications for natural gas, a $CO_2$ fraction free of hydrogen sulfide, and an $H_2S$ fraction which can be reacted to elemental sulfur without an intermediate post-treatment step.

Upon further study of the specification and appended claims, further objects and advantages of this invention will become apparent to those skilled in the art.

These objects are attained according to the invention by feeding dried raw gas to a rectification stage for separating said gas into a hydrocarbon-rich fraction containing some acidic components ($CO_2$, $H_2S$), as the head product, and a fraction consisting essentially of said acidic components, as the bottoms product; separating, in a first scrubbing column, the acidic components from the head product with a physical scrubbing medium; vaporizing the bottoms product; and, in a second scrubbing column, scrubbing resultant vaporized bottoms product with the same physical scrubbing medium to selectively remove the sulfur-containing compounds, and discharging the thus-scrubbed gas from the second scrubbing column as $CO_2$ under pressure.

This system according to this invention comprising a rectifying stage to form a hydrocarbon-rich fraction, for example of methane, and a hydrocarbon-depleted fraction containing sour gases (i.e., acidic components), combined with the subsequent scrubbing stages for the two fractions in two scrubbing columns but with the same, physical scrubbing medium selective for $H_2S$ vis a vis $CO_2$, results, synergistically in unexpectedly high yields and purities of a hydrocarbon product fraction, a $CO_2$ product fraction, and an $H_2S$ product fraction. The purity of the $H_2S$ and $CO_2$ fractions permit, on the one hand, the introduction of the $H_2S$ fraction directly to a Claus installation for further processing and, on the other hand, the utilization of the pressurized $CO_2$, for example, in tertiary petroleum recovery to increase the yield of petroleum.

According to the invention, the rectification is conducted under a pressure lying below the critical pressure at all locations of the column. In particular, the pressure is maintained at values of between 40 and 65 bar, preferably between 45 and 58 bar. Thus, the critical pressure of the condensate is nowhere exceeded within the column, so that the condensate remains in the liquid phase. The temperature of the overhead product is preferably in the range of about $-45°$ — $-56°$ C. whereas the temperature of the sump liquid is preferably about $+10°$ — $+40°$ C.

According to a preferred aspect of this invention, the overhead product from the rectifying column, after separation of the sulfur-containing components, especially $H_2S$ and COS, is cooled and freed of $CO_2$ be low ambient temperature. The working temperature is defined by refrigeration cycle.

The separation of $H_2S$ and COS is conducted in most cases in a lower section of a scrubbing column, into which $CO_2$-loaded scrubbing medium is introduced. The desulfurized gas then flows further upwardly into the upper section of the column, the same but non-$CO_2$-loaded scrubbing agent being used to scrub out $CO_2$ up to a content corresponding to the purity requirements of the resultant gas, e.g., less than 2 mol% $CO_2$ but using as fuel gas, or some ppm if the gas is handled in a following liquefaction. Due to the lower $CO_2$ solubility in scrubbing agent selective for $H_2S$, it is advantageous to lower the operating temperature in the upper column section during this step to increase $CO_2$ solubility, as indicated above.

According to another preferred aspect of this process of this invention, the $CO_2$-loaded scrubbing medium withdrawn from the upper section of the first scrubbing column is divided and used, in part, for desulfurizing the rectification overhead product in the lower section of the first scrubbing column and, in part, for the absorption of sulfur-containing components in the second scrubbing column. By this twin use of the $CO_2$-loaded scrubbing medium, a substantial increase in the ultimate yield of $CO_2$ is obtained. Furthermore, it is preferred that a portion of the $CO_2$ overhead gaseous product produced in the second scrubbing column be liquefied and reintroduced into the scrubbing column for condensing scrubbing medium vapors which would otherwise escape. The scrubbing medium withdrawn from the bottom of the second scrubbing column contains the entire amount of scrubbed-out $H_2S$ and COS, as well as a considerable content of dissolved $CO_2$ owing to the high $CO_2$ partial pressure in the entering gas. This second scrubbing column is preferably operated at about $0°-+30°$ C. and under a pressure of 45-75 bar.

To increase the $H_2S$ concentration and the yield in $CO_2$, another preferred aspect of the invention provides that the loaded scrubbing medium from the bottom of the second scrubbing column be heated under pressure and the thus-liberated gaseous fraction be recycled into the scrubbing column. For compensation of the pressure drop in the recycle circuit, the loaded scrubbing medium is pumped to a compensating pressure.

According to another preferred aspect of the process of this invention, the scrubbing medium withdrawn from the first scrubbing column, loaded with the sulfur-containing components, can be partially expanded to preferably about 20-40% of the pressure of the feed gas and the thus-liberated gaseous fraction can, after recompression, by recycled into preferably the lower section of the scrubbing column. By this intermediate expansion, hydrocarbons, in particular, still present in the scrubbing medium, are liberated, which are then again subjected to the scrubbing operation together with the concomitantly liberated sour gases.

According to a further preferred aspect of the invention, the resultant partially expanded scrubbing medium of the first scrubbing column and the heated scrubbing medium of the second scrubbing column can be further expanded and the thus-liberated fraction, rich in $H_2S$, can be withdrawn. For a further enrichment of hydrogen sulfide, the expanded scrubbing medium streams can be fed to an $H_2S$ enrichment step prior to regeneration; in this case, $CO_2$ can additionally be stripped off with the use of an inert gas. Such a process is known to those skilled in the art from physical scrubbing processes, e.g. low temperature wash using methanol as scrubbing liquid (e.g. U.S. Pat. No. 4,050,909).

If the source of raw gas is not under sufficient pressure, the raw gas is compressed to an optimum operating pressure. In this operation, energy is not wasted, since the $CO_2$ and methane are processed under pressure.

Suitable scrubbing media for the process of this invention comprise all physical absorbents exhibiting, in particular, selectivity for $H_2S$ and COS versus $CO_2$. Such media include but are not limited to the already recited polyethylene glycol ether, N-methylpyrrolidone and propylene carbonates, and also, for example, toluene and xylene.

Toluene proved to be especially preferred when COS is present in the raw gas to be purified, since it displays a higher absorbability effect for COS than the other scrubbing agents.

This invention is applicable to the treatment of all gases containing $H_2S$, $CO_2$ and light hydrocarbons, especially methane, but also including $N_2$ and He.

In particular, the invention is applicable to raw gases containing more than 50 mol% acid gases.

BRIEF DESCRIPTION OF FIGURE

The FIGURE is a schematically illustrated preferred comprehensive embodiment of the several aspects of the invention.

DETAILED DISCUSSION

At 1, raw gas is fed under a pressure of above 55 bar, for example 100 bar, to a drying stage 2. A raw gas of the following composition is to be processed:

| | |
|---|---|
| $N_2$ | 3 mol % |
| $CH_4$ | 23 mol % |
| $CO_2$ | 70 mol % |
| $H_2S$ | 4 mol % |

For drying purposes, the raw gas is preferably conducted over adsorbers having adsorption agents selective for $H_2O$, e.g., molecular sieves. The amount of gas after drying is 10,000 kmol/h; the temperature is 35° C.

The thus-dried raw gas is conducted via conduit 3 to a turbine 4 for expansion to a pressure lying somewhat below the critical pressure of this raw gas, for example 56 bar. During this step, cooling and partial condensation occurs. The condensate obtained during expansion in an amount of 925 kmol/h and a composition of

| | |
|---|---|
| $N_2$ | 0.6 mol % |
| $CH_4$ | 7.6 mol % |
| $CO_2$ | 86.0 mol % |
| $H_2S$ | 5.8 mol % | is withdrawn via conduit 6 from phase separator 5 and fed into the lower section of a rectifying column 7. The gaseous phase from the phase separator is passed via conduit 8 to heat exchanger 9 where it is cooled in indirect heat exchange against cold overhead product gas from column 7, as well as against external refrigeration (10), thereby achieving further condensation. The resultant two-phase mixture is fed to the rectifying column 7 above the midpoint.

By rectification, the feedstreams are separated into an overhead product having a composition of:

| | |
|---|---|
| $N_2$ | 9.7 mol % |
| $CH_4$ | 73.6 mol % |
| $CO_2$ | 16.1 mol % |
| $H_2S$ | 0.6 mol % | in a quantity of 3076 kmol/h at a temperature of $-56°$ C., and into a bottoms product having a composition of:

| | |
|---|---|
| $N_2$ | 0.01 mol % |
| $CH_4$ | 0.53 mol % |
| $CO_2$ | 93.96 mol % |
| $H_2S$ | 5.50 mol % | and at a temperature of about $+18°$ C.

The external cold required at the head of the rectifying column for rectification is provided, for example, by vaporizing ethane in condenser 11; the reboiler 12 of the column is suitably heated by a $C_3$-refrigeration cycle (not shown), wherein the compressor pressure is set to enable the refrigerant to be condensed while the column bottoms are being vaporized in the reboiler.

After the methane-rich head product from the rectifying column 7 is withdrawn via conduit 13 and heated against raw gas in heat exchanger 9, this gas is treated in the lower section of a scrubbing column 14 with a scrubbing medium selective for $H_2S$ as against $CO_2$ and $CH_4$. In this embodiment, there is used as the scrubbing medium, toluene which has been preloaded with $CO_2$ in the upper $CO_2$ scrubbing section. This toluene-$CO_2$ mixture is branched off conduit 18 and introduced via conduit 19 into the lower section of the scrubbing column, where $H_2S$ and COS are scrubbed out from the gas. In the upper column section, $CO_2$ is subsequently scrubbed out with the same scrubbing medium except to the extent that a residual content of $CO_2$ is permitted according to the purity requirements for the thus-obtained fuel gas. The amount of scrubbing medium used in the $H_2S$ scrubbing step in the lower section is 65 t/h, whereas the amount used in the $CO_2$ removal step in the upper section of the column is 300 t/h, the latter being regenerated toluene cooled by external refrigeration in cooler 16. By means of this process, it is also possible to obtain a fuel having only several ppm, e.g., 10–100 of $CO_2$, which would be important if the gas were passed to a downstream low-temperature plant, for example for the separation of $N_2$. The heat of solution developed in the scrubbing column is removed, in part, by heat exchange with the cold toluene and, in part, by a cooling stage, not shown. A methane-rich fraction having the following composition is withdrawn overhead from the scrubbing 14 in conduit 17:

| | |
|---|---|
| $N_2$ | 12.3 mol % |
| $CH_4$ | 86.7 mol % |
| $CO_2$ | 1.0 mol % |
| $H_2S$ | 4 ppm |

The total amount of the methane fraction is 2422.7 kmol/h. After being heated in exchanger 56 against toluene, the gas is available under a pressure of 53 bar.

After the scrubbing medium, loaded with $CO_2$, withdrawn from column 14, is divided, with a portion being utilized via conduit 19 for scrubbing out $H_2S$ from the methane-rich gas; the remainder is conducted via conduit 18 to a second scrubbing column 20.

The scrubbing medium loaded with both $CO_2$ and $H_2S$, withdrawn from the bottom of the scrubbing column via conduit 21, is first expanded to an intermediate pressure (22) and the thus-liberated gas—preferably methane and $CO_2$—is withdrawn from a phase separator 23 and passed via conduit 24 to compressor 25 where it is recompressed to the pressure of the raw gas upstream of the scrubbing column 14 and is admixed with said raw gas.

The $CO_2$-rich condensate obtained at the bottom of the rectifying column 7 is withdrawn via conduit 26, pumped by means of a pump 27 to a pressure of 68 bar, and thereafter vaporized (28), thereby withdrawing the heat from said $C_3$-refrigeration cycle. In the second scrubbing column 20, the vaporized liquid is scrubbed with the scrubbing medium discharged from the $CO_2$-removal section of the first scrubbing column. The resultant scrubbed gaseous $CO_2$ withdrawn from the head of the scrubbing column 20 via conduit 29 is obtained under a pressure of 67 bar, and is practically free of sulfur-containing compounds.

Due to the high operating temperature, e.g., 47° C., of the scrubbing column 20, which must lie above the $CO_2$ liquefaction temperature of 26° C., the scrubbing medium has such a high vapor pressure that a relatively large loss of scrubbing medium vapors would ordinarily occur. In order to recover these scrubbing medium vapors, the desulfurized $CO_2$ is cooled against an external refrigeration cycle in exchanger (30) and partially condensed during this step. The condensate at a temperature of 26° C. is passed from the bottom of a separator 31 via conduit 32 to the head of the scrubbing column 20 above the scrubbing medium feed and serves to condense the scrubbing medium vapors. At the same time, the liquid $CO_2$ can be used for the refrigeration balance.

The $CO_2$ withdrawn in the gaseous phase from phase separator 31 at a rate of 5886 kmol/h, has the following composition:

| | |
|---|---|
| $N_2$ | 0.02 mol % |
| $CH_4$ | 1.97 mol % |
| $CO_2$ | 98.01 mol % |
| $H_2S$ | 10 ppm |

The purified $CO_2$ is subsequently further compressed in a compressor 33 coupled to the expansion turbine and discharged as product via conduit 34.

The scrubbing medium withdrawn via conduit 35 from the bottom of the scrubbing column 20 contains not only essentially the entire amount of $H_2S$ and COS fed with the $CO_2/H_2S$ mixture, but also a very large amount of dissolved $CO_2$ due to the high pressure. To recover the $CO_2$ and simultaneously to increase the $H_2S$ concentration in the $H_2S$ fraction, the loaded scrubbing medium is heated under pressure in heat exchanger 36 against regenerated scrubbing medium. The thus-liberated gas, mostly $CO_2$, is recycled from the head of separator 37 directly via conduit 38 to the scrubbing column 20. To compensate for the pressure drop in the phase separator 37, a pump 39 is employed upstream thereof.

The two $H_2S$-containing scrubbing medium streams obtained from the bottom of separator 23 via conduit 40 and from the bottom of separator 37 via conduit 41 are both expanded (42, 43) to a pressure of 4 bar and passed to phase separator 45. In the latter separator, gaseous $H_2S$ is withdrawn via conduit 44 from the head of the phase separator. The resultant expanded liquid streams of scrubbing medium are passed via conduit 46 to heat exchanger 47, wherein they are heated against regenerated scrubbing medium, and from there to the upper part of a stripping column 48 where the remaining dissolved gases $CO_2$ and $H_2S$ are driven off. In this stripping column, the scrubbing medium is vaporized in reboiler 49, and the vapors thereof are condensed in the head condenser 50. The residual sour gas withdrawn from the head of column 48 via conduit 51 has the following composition:

| | |
|---|---|
| $N_2$ | 0 |
| $CH_4$ | 5.0 mol % |
| $CO_2$ | 71.4 mol % |
| $H_2S$ | 23.6 mol % |

The total amount is 1691.3 kmol/h.

The regenerated scrubbing medium is withdrawn via conduit 52 with pump 53 from the bottom of the stripping column 48. A portion of the regenerated scrubbing medium is cooled via conduit 54 in heat exchanger 47 while the other portion is cooled via conduit 55 in heat exchanger 36. The two regenerated streams of scrubbing medium are combined in conduit 15 and introduced into the head of the scrubbing column 14.

If heavier hydrocarbons are contained in the raw gas, they can be separated by an additional conventional rectification arranged upstream of the sour gas separation.

It is possible by the process of this invention to fractionate raw gas in such a way that there are obtained simultaneously a salable methane fraction having an $H_2S$ content of 4 ppm, a $CO_2$ fraction of a 98% purity, as well as an $H_2S$ fraction which, in a Claus plant, can be reacted to elemental sulfur. A further special advantage of this system is that besides $H_2S$, COS can also be completely scrubbed out. This is of significance insofar as COS, during the drying step with adsorbers, can be formed catalytically from $H_2S$ and is very difficult to scrub out simultaneously with chemical scrubbing steps, e.g., COS is not washed out in scrubbing processes selective for $H_2S$, such as, for example, amine scrubbing methods.

The preceding example can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the removal of acidic components comprising $CO_2$ and $H_2S$, from $CO_2$-rich, hydrocarbon-containing raw gas wherein the raw gas is scrubbed under pressure with a physical scrubbing medium selective for $H_2S$ and COS as compared to $CO_2$ and hydrocarbons, and the resultant loaded scrubbing medium is regenerated and reused, the improvement comprising subjecting dry raw gas to rectification to form a hydrocarbon-rich fraction containing acidic components, as rectification overhead product, and a fraction consisting essentially of acidic components, as rectification bottoms product; scrubbing said rectification overhead product in a first scrubbing column to absorb the acidic components in the physical scrubbing medium to form a first scrubbing column bottoms product; vaporizing the rectification bottoms product; withdrawing partially loaded scrubbing medium from said first scrubbing column and scrubbing the vaporized rectification bottoms product in a second scrubbing column with said partially loaded scrubbing medium to selectively absorb the sulfur-containing compounds to form a loaded scrubbing medium; and discharging resultant scrubbed gas from the second scrubbing column as $CO_2$ overhead product under pressure and essentially free of sulfur compounds.

2. A process according to claim 1, wherein the rectification is conduited under a pressure below the critical pressure of the raw gas throughout the column.

3. A process according to claim 2, wherein the pressure is maintained at 40–65 bar.

4. A process according to claim 2, wherein the pressure is maintained at 45–58 bar.

5. A process according to claim 1, wherein the rectification overhead product gas is treated in said first scrubbing column to remove $H_2S$ and COS, and is then cooled and freed of $CO_2$ at lower temperatures.

6. A process according to claim 1, wherein the first scrubbing column comprises an upper zone and a lower zone, and the sulfur-containing components are scrubbed out in the lower zone, and the resultant scrubbed gas from said lower zone is further scrubbed in the upper zone at temperatures lower than the temperature of the lower zone, thereby removing $CO_2$.

7. A process according to claim 6, wherein resultant $CO_2$-loaded scrubbing medium from the bottom of the upper zone of the first scrubbing column is divided and employed in part as scrubbing medium to desulfurize the rectification overhead product in the first scrubbing column and, in part, as scrubbing medium for the absorption of sulfur-containing components in the second scrubbing column.

8. A process according to claim 7, further comprising liquefying, in part, said $CO_2$ overhead product discharged from the second scrubbing column, and reintroducing the resultant liquid $CO_2$ into the scrubbing column to condense scrubbing medium vapors.

9. A process according to claim 8, further comprising heating under pressure the loaded scrubbing medium from the second scrubbing column, to form a gaseous and liquid fraction thereof, and recycling the thus-liberated gaseous fraction to the second scrubbing column.

10. A process according to claim 9, further comprising partially expanding the first scrubbing column bottoms product loaded with the sulfur-containing components, and recycling resultant liberated gaseous fraction into the first scrubbing column.

11. A process according to claim 10, further comprising partially expanding the first scrubbing column bottoms product loaded with the sulfur-containing components, and recycling resultant liberated gaseous fraction into the first scrubbing column.

12. A process according to claim 11, comprising further expanding resultant partially expanded liquid scrubbing medium from the first scrubbing column and resultant heated liquid scrubbing medium from the second scrubbing column, and withdrawing resultant $H_2S$-rich gaseous fraction therefrom.

13. A process according to claim 1, further comprising liquefying, in part, said $CO_2$ overhead product discharged from the second scrubbing column, and reintroducing the resultant liquid $CO_2$ into the scrubbing column to condense scrubbing medium vapors.

14. A process according to claim 1, further comprising heating under pressure the loaded scrubbing medium from the second scrubbing column, to form a gaseous and liquid fraction thereof, and recycling the thus-liberated gaseous fraction to the second scrubbing column.

15. A process according to claim 14, further comprising partially expanding the first scrubbing column bottoms product loaded with the sulfur-containing components, and recycling resultant liberated gaseous fraction into the first scrubbing column.

16. A process according to claim 15, comprising further expanding resultant partially expanded liquid scrubbing medium from the first scrubbing column and resultant heated liquid scrubbing medium from the second scrubbing column, and withdrawing resultant $H_2S$-rich gaseous fraction therefrom.

17. A process according to claim 16, further comprising introducing resultant expanded liquid scrubbing medium stream to an $H_2S$-enrichment stage.

18. A process according to claim 1, further comprising partially expanding the first scrubbing column bottoms product loaded with the sulfur-containing components, and recycling resultant liberated gaseous fraction into the first scrubbing column.

19. A process according to claim 1, wherein said raw gas contains COS.

20. A process according to claim 19, wherein the dry raw gas is obtained by the preceding step of passing raw gas through an adsorber.

21. A process according to claim 19, wherein said scrubbing medium is toluene.

22. A process according to claim 1, wherein the dry raw gas is obtained by the preceding step of passing raw gas through an adsorber.

23. A process according to claim 1, wherein said scrubbing medium is polyethylene glycol ether, N-methylpyrrolidone, propylene carbonate, toluene or xylene.

* * * * *